(12) United States Patent
Hao et al.

(10) Patent No.: US 11,541,032 B2
(45) Date of Patent: Jan. 3, 2023

(54) COMPOSITION CONTAINING SUMO INHIBITOR AND APPLICATION

(71) Applicant: CHINA PHARMACEUTICAL UNIVERSITY, Nanjing (CN)

(72) Inventors: Haiping Hao, Nanjing (CN); Hong Wang, Nanjing (CN); Jiyu Zhou, Nanjing (CN); Guangji Wang, Nanjing (CN); Shuang Cui, Nanjing (CN); Xiaojie Pan, Nanjing (CN); Yitong Guo, Nanjing (CN); Ningning Huang, Nanjing (CN)

(73) Assignee: CHINA PHARMACEUTICAL UNIVERSITY, Nanjing (CN)

(*) Notice: Subject to any disclaimer, the term of this patent is extended or adjusted under 35 U.S.C. 154(b) by 239 days.

(21) Appl. No.: 16/960,226

(22) PCT Filed: Nov. 22, 2019

(86) PCT No.: PCT/CN2019/120210
§ 371 (c)(1),
(2) Date: Jul. 6, 2020

(87) PCT Pub. No.: WO2020/119424
PCT Pub. Date: Jun. 18, 2020

(65) Prior Publication Data
US 2020/0368199 A1    Nov. 26, 2020

(30) Foreign Application Priority Data
Dec. 14, 2018    (CN) .......................... 201811534024.X

(51) Int. Cl.
| | | |
|---|---|---|
| *A61K 31/357* | (2006.01) | |
| *A61K 31/201* | (2006.01) | |
| *A61K 31/42* | (2006.01) | |
| *A61K 31/55* | (2006.01) | |
| *A61K 31/575* | (2006.01) | |

(52) U.S. Cl.
CPC .......... *A61K 31/357* (2013.01); *A61K 31/201* (2013.01); *A61K 31/42* (2013.01); *A61K 31/55* (2013.01); *A61K 31/575* (2013.01)

(58) Field of Classification Search
CPC .................................................... A61K 31/357
See application file for complete search history.

(56) References Cited

FOREIGN PATENT DOCUMENTS

CN         106974916 A    *    7/2017    ........... A61K 31/155

OTHER PUBLICATIONS

Fang et al., "Downregulation of UBC9 promotes apoptosis of activated human LX-2 hepatic stellate cells by suppressing the canonical NF-KB signaling pathway", PLoS ONE 12(3): e0174374, Mar. 30, 2017 (Year: 2017).*
Wong et al., "Direct and/or Indirect Roles for SUMO in Modulating Alpha-synuclein Toxicity", Biomolecules, vol. 5, pp. 1617-1716, Jul. 24, 2015 (Year: 2015).*
Yuan et al., "9-cis-retinoic acid elevates MRP3 expression by inhibiting SUMOlyation of RXR-alpha to alleviate cholestatic liver injury", Elsevier, Jun. 18, 2018 (Year: 2018).*
Gao et al., "Effects of farnesoid-X-receptor-SUMOlyation mutation on myocardial ischemia/reperfusion injury in mice", Elsevier, Aug. 8, 2018 (Year: 2018).*

* cited by examiner

*Primary Examiner* — Daniel R Carcanague
*Assistant Examiner* — Gillian A Hutter
(74) *Attorney, Agent, or Firm* — CBM Patent Consulting, LLC

(57) ABSTRACT

A composition containing SUMO inhibitor, and belongs to the technical field of medicine includes FXR agonist and SUMO inhibitor. In activated hepatic stellate cells, the FXR agonist does not have an effect in inhibiting the activation of hepatic stellate cells. After the FXR agonist and the SUMO inhibitor are compounded according to the present invention, the activation of hepatic stellate cells can also be inhibited for those cells under activated state. Of note, the hepatic stellate cells of an individual with hepatic fibrosis symptoms have been in an activated state, therefore a good anti-fibrotic effect cannot be achieved by using the FXR agonist alone.

8 Claims, 12 Drawing Sheets

Specification includes a Sequence Listing.

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: It is synthesized.

<400> SEQUENCE: 1
tggactcata cagcaaacag aga                                            23

<210> SEQ ID NO 2
<211> LENGTH: 23
<212> TYPE: DNA
<213> ORGANISM: Artificial Sequence
<220> FEATURE:
<223> OTHER INFORMATION: It is synthesized.

<400> SEQUENCE: 2
gtctgaaacc ctggaagtct ttt                                            23

<210> SEQ ID NO 3
<211> LENGTH: 17
<212> TYPE: DNA
<213> ORGANISM: Artificial Sequence
<220> FEATURE:
<223> OTHER INFORMATION: It is synthesized.

<400> SEQUENCE: 3
cctggagcag ccctcgt                                                   17

<210> SEQ ID NO 4
<211> LENGTH: 22
<212> TYPE: DNA
<213> ORGANISM: Artificial Sequence
<220> FEATURE:
<223> OTHER INFORMATION: It is synthesized.

<400> SEQUENCE: 4
```
aacactgtat gcaaaccgag ga                                              22

<210> SEQ ID NO 5
<211> LENGTH: 20
<212> TYPE: DNA
<213> ORGANISM: Artificial Sequence
<220> FEATURE:
<223> OTHER INFORMATION: It is synthesized.

<400> SEQUENCE: 5
gctccatcct ggcttctcta                                                 20

<210> SEQ ID NO 6
<211> LENGTH: 20
<212> TYPE: DNA
<213> ORGANISM: Artificial Sequence
<220> FEATURE:
<223> OTHER INFORMATION: It is synthesized.

<400> SEQUENCE: 6
tagaagcatt tgcggtggac                                                 20

<210> SEQ ID NO 7
<211> LENGTH: 20
<212> TYPE: DNA
<213> ORGANISM: Artificial Sequence
<220> FEATURE:
<223> OTHER INFORMATION: It is synthesized.

<400> SEQUENCE: 7
aacggcacag tcaaggctga                                                 20

<210> SEQ ID NO 8
<211> LENGTH: 22
<212> TYPE: DNA
<213> ORGANISM: Artificial Sequence
<220> FEATURE:
<223> OTHER INFORMATION: It is synthesized.

<400> SEQUENCE: 8
acgccagtag actccacgac at                                              22

<210> SEQ ID NO 9
<211> LENGTH: 20
<212> TYPE: DNA
<213> ORGANISM: Artificial Sequence
<220> FEATURE:
<223> OTHER INFORMATION: It is synthesized.

<400> SEQUENCE: 9
gcacgctgat cagacagcta                                                 20

<210> SEQ ID NO 10
<211> LENGTH: 20
<212> TYPE: DNA
<213> ORGANISM: Artificial Sequence
<220> FEATURE:
<223> OTHER INFORMATION: It is synthesized.

<400> SEQUENCE: 10
caggagggtc tgttggtctg                                                 20

<210> SEQ ID NO 11
<211> LENGTH: 20
<212> TYPE: DNA
<213> ORGANISM: Artificial Sequence

```
<220> FEATURE:
<223> OTHER INFORMATION: It is synthesized.

<400> SEQUENCE: 11
gtacctgaag ggcacgatcc                                              20

<210> SEQ ID NO 12
<211> LENGTH: 21
<212> TYPE: DNA
<213> ORGANISM: Artificial Sequence
<220> FEATURE:
<223> OTHER INFORMATION: It is synthesized.

<400> SEQUENCE: 12
gtgaagtctt ggagccctgg t                                            21

<210> SEQ ID NO 13
<211> LENGTH: 21
<212> TYPE: DNA
<213> ORGANISM: Artificial Sequence
<220> FEATURE:
<223> OTHER INFORMATION: It is synthesized.

<400> SEQUENCE: 13
gcacccagca tgaagatcaa g                                            21

<210> SEQ ID NO 14
<211> LENGTH: 24
<212> TYPE: DNA
<213> ORGANISM: Artificial Sequence
<220> FEATURE:
<223> OTHER INFORMATION: It is synthesized.

<400> SEQUENCE: 14
tctgctggaa ggtagacagc gaag                                         24

<210> SEQ ID NO 15
<211> LENGTH: 20
<212> TYPE: DNA
<213> ORGANISM: Artificial Sequence
<220> FEATURE:
<223> OTHER INFORMATION: It is synthesized.

<400> SEQUENCE: 15
ttgatggcaa caatctccac                                              20

<210> SEQ ID NO 16
<211> LENGTH: 20
<212> TYPE: DNA
<213> ORGANISM: Artificial Sequence
<220> FEATURE:
<223> OTHER INFORMATION: It is synthesized.

<400> SEQUENCE: 16
cgtcccgtag acaaaatggt                                              20
```

COMPOSITION CONTAINING SUMO INHIBITOR AND APPLICATION

This application claims priority to Chinese Patent Application Serial No. 201811534024.X, entitled "Composition Containing SUMO inhibitor and Application", filed with the National Intellectual Property Administration, PRC (China) on Dec. 14, 2018, which is incorporated herein by reference in its entirety.

TECHNICAL FIELD

The present invention relates to the technical field of medicine, and more particularly relates to a composition containing SUMO inhibitor and application.

BACKGROUND ART

The incidence rate of liver diseases, especially viral hepatitis, fatty liver diseases, liver fibrosis, liver cancer, etc., is high worldwide. For example, the incidence rate of nonalcoholic fatty liver in common adults in Europe and America is 20 to 33%, and reaches 60 to 90% in obese people, and the prevalence rate in Chinese normal adults is about 15% (Fan J G, Farrell G C. Epidemiology of nonalcoholic fatty liver disease in China. Journal of hepatology, 2009, 50 (1): 204-10.). Liver fibrosis is a pathological condition, and refers to excessive deposition of fibrous connective tissues of the liver. Liver fibrosis is an intermediate link of further development of chronic liver diseases such as chronic viral hepatitis, metabolic disorders and chronic alcoholic/nonalcoholic fatty liver to liver cirrhosis. Liver fibrosis is a common important characteristic of the chronic liver diseases, and 25 to 40% of patients with chronic liver diseases finally develop into patients with liver cirrhosis or even liver cancer. Recent studies have shown that the liver fibrosis is a reversible lesion while the liver cirrhosis is an irreversible lesion. Therefore, inhibition, prevention and reversal of liver fibrosis are central links in treatment of various chronic liver diseases. Hepatic stellate cells (HSCs) are the key cells for mediating development of the liver fibrosis. The HSCs are in a quiescent state in healthy liver. When being stimulated by pathological factors, the HSCs are activated into a fibroblast phenotype with a proliferative capacity. The HSCs of this phenotype can secrete a large number of fibrosis factors and collagen fibers, and finally induce the development of liver fibrosis and cirrhosis. Therefore, the HSCs are determinants of the development of the liver fibrosis, and inhibition of activation of the HSCs is an important strategy to treat and reverse liver fibrosis.

The research and development of medicine against liver fibrosis is a hot spot of the research and development of hepatoprotective medicine currently, and certain research progress has been made at the same time. The currently claimed therapeutic medicine related to prevention and treatment of the liver fibrosis mainly includes the following categories: 1) traditional Chinese herbal medicines and extracts thereof, such as rhizoma curcumae longae, resveratrol, silymarin, allocryptopine and salts thereof (Authorization Announcement No.: CN10132721B); 2) chemicals and preparations thereof, such as pirfenidone and creatinine compositions (Authorization Announcement No.: CN103550242B), cleistanone derivatives (Authorization Announcement No.: CN104095857B); and 3) biological agents including recombinant proteins and gene medicine, the recombinant proteins including a TGFβ1-inhibitory peptide (Authorization Announcement No.: CN1203091C), IL-4 (Authorization Announcement No.: CN101318013B), a monoclonal antibody HAb18GC2 and heavy-chain and light-chain variable region genes and polypeptides thereof (Authorization Announcement No.: CN100586960C), and the gene medicine including a hepatocyte nuclear factor 1α gene (Authorization Announcement No.: CN102552935B), a gene medicine for expressing a hepatopoietin (Application No.: 200610145523.0), and a human hepatocyte growth factor gene (Authorization Announcement No.: CN1142272C). Although there is much therapeutic medicine, specific medicine for the liver fibrosis has not been found at present. Therefore, it is a hard development direction in the future to find effective anti-hepatic fibrosis medicine.

Farnesoid X receptor (FXR), also called as NR1H4 (Nuclear Receptor Subfamily 1, Group H, Member 4), is a member of a nuclear receptor superfamily. Since the receptor was cloned in 1995, more and more functions of this receptor have been recognized. FXR plays an important role in physiological processes such as bile acid, lipid and glucose metabolism, and also has a regulation effect on various pathological processes. FXR promotes liver regeneration through FXR-FGF15/19 signaling pathway. FXR exerts anti-inflammatory effect through FXR/NF-κB negative feedback loop (Wang Y D, Chen W D, Wang M, et al. Farnesoid X receptor antagonizes nuclear factor kappaB in hepatic inflammatory response. Hepatology, 2008, 48(5): 1632-43.). FXR achieves anti-autophagy effect by blocking formation of a CREB-CRTC2 complex and inhibiting expression of autophagy-related genes (Seok S, Fu T, Choi S E, et al. Transcriptional regulation of autophagy by an FXR-CREB axis. Nature 2014; 516:108-U274.). Additionally, FXR is closely related to formation of liver tumor. FXR-/-mice all spontaneously developed liver tumors by 15 months of normal feeding while wild-type mice of the same age did not exert the same changes (Yang F, Huang X, Yi T, et al. Spontaneous development of liver tumors in the absence of the bile acid receptor farnesoid X receptor. Cancer Res 2007; 67:863-867.). These studies show that FXR is closely related to the development of various liver diseases. FXR agonist is a major research strategy for the development of hepatoprotective anti-fibrosis medicine. There are a number of related patent applications (Wang H, He Q, Wang G, et al. FXR modulators for enterohepatic and metabolic diseases. Expert Opin Ther Pat. 2018 Nov.; 28(11):765-782), for example, CN201210482982.3 (Application No.) provides application of altenusin compounds and pharmaceutically acceptable salts thereof to preparation of medicine for treating FXR-mediated diseases, CN201180067346.8 and CN201080043283.8 (Application No.) disclose application of an FXR activity modulator to a medicine composition, and all of them have been granted. Additionally, obeticholic acid (OCA), as strong FXR agonist, has just completed the clinical Phase III study on its anti-NASH medicine efficacy. The results showed that fibrosis symptoms of 21.0% of patients in a group taking 25 mg daily OCA had been relieved (fibrosis symptoms of 10.6% of patients in a placebo group had been relieved), suggesting that the OCA has certain relieving and treatment effects on the liver fibrosis, but how to improve its anti-hepatic fibrosis activity is an important scientific problem. Additionally, as anti-primary biliary cirrhosis (PBC) medicine, it was approved for marketing by the U.S. FDA in May, 2016 (Markham A, Keam S J. Obeticholic Acid: First Global Approval. Drugs. 2016 August; 76(12):1221-6.), and has become the first successfully marketed medicine targeting FXR.

Results from previous pre-clinical studies in animal fibrosis models have shown that OCA and other FXR agonists exert excellent beneficial effects against fibrosis by inhibiting the activation of HSCs via activating the FXR signaling in HSCs (Fiorucci S, Antonelli E, Rizzo G, et al. The nuclear receptor SHP mediates inhibition of hepatic stellate cells by FXR and protects against liver fibrosis. Gastroenterology. 2004 November; 127(5):1497-512. Fiorucci S1, Rizzo G, Antonelli E, et al. A farnesoid x receptor-small heterodimer partner regulatory cascade modulates tissue metalloproteinase inhibitor-1 and matrix metalloprotease expression in hepatic stellate cells and promotes resolution of liver fibrosis. J Pharmacol Exp Ther. 2005 August; 314(2):584-95.). However, recent studies revealed that the FXR agonist does not have an effect on the FXR signaling pathway of activated HSCs and exert marginal effect on the activation of the HSCs (Kowdley K V, Luketic V, Chapman R, et al. A randomized trial of obeticholic acid monotherapy in patients with primary biliary cholangitis. Hepatology. 2018 May; 67(5):1890-1902.). Additionally, results of two recent clinical studies have shown that compared with a placebo, the FXR agonist, such as OCA, did not have a significant improvement effect on the liver fibrosis index of PBC patients (Nevens F, Andreone P, Mazzella G, et al. A Placebo-Controlled Trial of Obeticholic Acid in Primary Biliary Cholangitis. N Engl J Med. 2016 Aug. 18; 375(7): 631-43; Kowdley K V, Luketic V, Chapman R, et al. A randomized trial of obeticholic acid monotherapy in patients with primary biliary cholangitis. Hepatology. 2018 May; 67(5):1890-1902.), and certain improvement effects were achieved on hepatic fibrosis symptoms of NASH patients, but its medicine efficacy was limited (improvement rate: OCA 21.0% vs placebo 10.6%).

SUMMARY OF THE INVENTION

An objective of the present invention is to provide a composition containing SUMO inhibitor. The composition includes FXR agonist and SUMO inhibitor, and can significantly inhibit activation of hepatic stellate cells and reduce deposition of collagen fibers to further significantly combat liver fibrosis.

The present invention provides the composition containing the SUMO inhibitor. The composition includes the FXR agonist and the SUMO inhibitor.

Preferably, the FXR agonist includes, but is not limited to, one or more of obeticholic acid, GW4064 and WAY-362450.

Preferably, the SUMO inhibitor includes, but is not limited to, spectinomycin and/or ginkgolic acid.

The present invention further provides application of the composition according to the above technical solution to preparation of anti-hepatic fibrosis medicine.

The present invention further provides application of the composition according to the above technical solution to preparation of anti-hepatic fibrosis symptom medicine.

The present invention further provides application of the composition according to the above technical solution to preparation of medicine for inhibiting activation of hepatic stellate cells.

The present invention further provides application of the composition according to the above technical solution to preparation of medicine for reducing deposition of collagen fibers.

Preferably, dose forms of the medicine independently include a tablet, a capsule, a granule, a pill, powder or an injection.

The present invention provides the composition containing the SUMO inhibitor. The composition includes the FXR agonist and the SUMO inhibitor. Under activated state of the hepatic stellate cells, the FXR agonist does not have an effect of inhibiting activation of the hepatic stellate cells. After the FXR agonist and the SUMO inhibitor are compounded according to the present invention, in the activated hepatic stellate cells, an FXR signaling pathway can be activated to inhibit the activation of the hepatic stellate cells and reduce the deposition of the collagen fibers, and liver fibrosis can be combated.

Additionally, the present invention has important significance that for healthy human bodies, the hepatic stellate cells are in a quiescent state and are responsive to FXR agonists. However, for fibrosis patients, the hepatic stellate cells have been in activated state with reduced responsiveness to FXR agonists, so that the FXR agonist cannot inhibit the activation of the hepatic stellate cells in the activated state. Therefore, in patient with fibrosis symptoms, pharmacological activity in combating liver fibrosis cannot be achieved through administration of FXR agonists. On the basis of explaining the underlying mechanism that activated hepatic stellate cells lose the responsiveness to the FXR agonist, the present invention creatively provides a combination mode, i.e., the application of the composition containing the SUMO inhibitor and the FXR agonist in preparation of the anti-hepatic fibrosis medicine. Due to the good responsiveness of activated hepatic stellate cells to the composition, the composition can significantly inhibit the activation of the hepatic stellate cells in the activated state. More importantly, for fibrotic patients, activation of the hepatic stellate cells can still be inhibited, the deposition of the collagen fibers can be reduced, and pharmacological effects in alleviating fibrosis can be achieved by taking the composition. Therefore, the composition has important practical values and application values for patients with the fibrosis symptoms.

DETAILED DESCRIPTION OF THE INVENTION

Figure 1A:
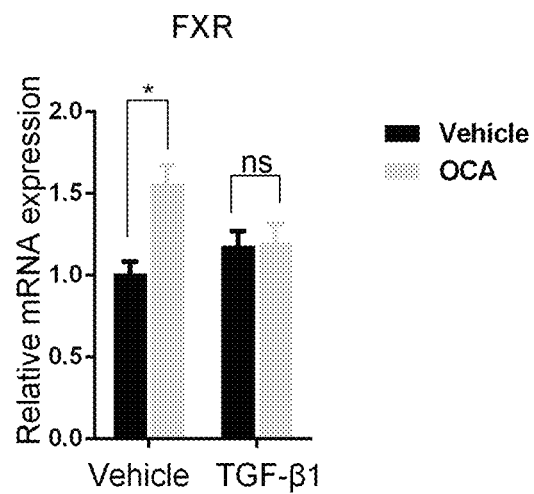
FIG. 1A is mRNA level analysis of Fxr in quiescent (vehicle) and activated (TGF-β) HSCs treated with OCA.

The present invention is further illustrated below in conjunction with embodiments and drawings.

The present invention provides a composition containing SUMO inhibitor. The composition includes FXR agonist and SUMO inhibitor. The present invention does not have specific limitation to a mass ratio of the FXR agonist to the SUMO inhibitor, and the mass ratio may be any value.

According to the present invention, the FXR agonist preferably includes, but is not only limited to, one or more of obeticholic acid, GW4064 and WAY-362450. The more specifically refers to two or more. According to the present invention, when there are two or more FXR agonists, all components are mixed according to any mass. The FXR agonists are not limited to the above three agonists according to the present invention, their sources are not specifically limited, and the FXR agonists preferably include various FXR agonists of a natural source, a semisynthetic source or a chemosynthetic source.

According to the present invention, the SUMO inhibitor preferably includes, but is not only limited to, spectinomycin and/or ginkgolic acid. According to the present invention, when the SUMO inhibitor preferably includes the spectinomycin and the ginkgolic acid, the spectinomycin and the ginkgolic acid are mixed according to any mass ratio. The SUMO inhibitors are not limited to the above two SUMO inhibitors, their sources are not specifically limited, and the SUMO inhibitors preferably include various SUMO inhibitors of a natural source, a semisynthetic source or a chemosynthetic source.

According to the present invention, hepatic stellate cells in activated state lose responsiveness to the FXR agonist, and the FXR agonist does not have an effect of inhibiting activation of the hepatic stellate cells. The SUMO inhibitor can significantly improve the responsiveness of the activated hepatic stellate cells to the FXR agonist, and can significantly enhance the inhibition effect of the FXR agonist on the activation of the hepatic stellate cells. The hepatic stellate cells of an individual with hepatic fibrosis symptoms have been in an activated state, and thus an expected anti-fibrotic effect cannot be achieved by using the FXR agonist alone. The composition of the FXR agonist and the SUMO inhibitor provided by the present invention can significantly inhibit the activation of the hepatic stellate cells and reduce deposition of collagen fibers to further combat liver fibrosis.

The present invention further provides application of the composition according to the above technical solution to preparation of anti-hepatic fibrosis medicine.

The present invention further provides application of the composition according to the above technical solution to preparation of anti-hepatic fibrosis symptom medicine.

The present invention further provides application of the composition according to the above technical solution to preparation of medicine for inhibiting activation of hepatic stellate cells.

The present invention further provides application of the composition according to the above technical solution to preparation of medicine for reducing deposition of collagen fibers.

According to the present invention, dose forms of the medicine independently include a tablet, a capsule, a granule, a pill, powder or an injection. Preparation methods of the above dose forms are not specifically limited according to the present invention. Conventional preparation methods for preparing corresponding dose forms and corresponding used auxiliary materials may be used for preparation.

According to the present invention, administration methods of the composition preferably include oral administration, intravenous injection, intravenous drip, intramuscular injection, and a combination of various administration modes.

The composition containing the SUMO inhibitor and application provided by the present invention are illustrated in detail below in conjunction with the embodiments, but they are not to be interpreted as limitation to the protection scope of the present invention.

Embodiment 1

Reason Analysis on Responsiveness Reduction of HSCs to FXR Agonist After Activation 1. Experiment Materials HSC-T6 cell line used in the present invention was purchased from Central South University Cell Bank.

OCA, GW4064 and WAY-362450 used in the present invention were purchased from MCE Company. TGF-β recombinant proteins were purchased from R&D Systems Company. Reverse transcription kits were purchased from Applied Biosystems Company. Trizol RNAiso plus was purchased from TAKARA Company. Used primers were synthesized by Life Invitrogen Company. SUMOylation ELISA detection kits were purchased from Epigentek Company. Other reagents were all commercially available.

2. Experiment Methods

2.1 HSC-T6 cell line culture and modeling

HSC-T6 cells, seeded and cultured in a proper density, were treated with TGF-β(10 mg/ml) or OCA (5 μM) or GW40064 (5 μM) or WAY-362450 (5 μM) for 12 h before collection.

2.2 Real-time quantitative PCR

2.2.1 Total RNA extraction of cell samples

1) After the cells were cleaned by PBS, 800 μl of a Trizol reagent was added. After repeated blowing by a pipette, the cells were transferred into an EP tube to be subjected to still standing for 5 min at the room temperature.

2) 160 μl of chloroform was added, and violent oscillation was performed for 15 sec. After still standing for 5 min at the room temperature, 12000 g centrifugation was performed for 15 min. The sample was divided into three layers including a bottom layer being a yellow organic phase, an upper layer being a colorless water phase, and a middle layer.

3) 300 μl of the upper layer water phase was carefully transferred into a new tube. 300 μl of isopropanol was added. After uniform mixing through reversing, still standing was performed for 10 min at the room temperature. Then, 12000 g centrifugation was performed for 10 min. Supernatant was abandoned.

4) RNA precipitates were washed by 1.0 ml of precooled 75% ethanol. Then, 12000 g centrifugation was performed for 5 min. Supernatant was abandoned to obtain total RNA. Redissolution was performed by 10 μl of DEPC water. After quantification, dilution was performed to 0.5 μg/μl.

2.2.2 Reverse transcription

RNA solutions and kit components were prepared into a system with a total volume of 20 μl according to a system proportion required in the specification, and a program temperature was set for reverse transcription. Specific proportion requirements are shown in Table 1:

TABLE 1

| Proportion for reverse transcription | |
|---|---|
| Reagent name | Dose |
| 10*RT Buffer | 2.0 μl |
| 25*dNTP Mix(100 mM) | 0.8 μl |
| 10*RT Random Primers | 2.0 μl |
| MultiScribeReverseTransscriptase | 1.0 μl |
| Rnase free dH$_2$O | 4.2 μl |
| Total | 10 μl |
| Total RNA | 10 μl |

Use conditions of reverse transcription are as follows:
Stage 1: reverse transcription at 37° C. for 15 min.
Stage 2: denaturation at 85° C. for 5 s.

2.2.3 PCR

A PCR system is shown in Table 2:

TABLE 2

| PCR system | |
|---|---|
| Reagent name | Dose |
| SYBR Green | 7.5 μl |
| PCR Forward Primer (10 μM) | 1.0 μl |
| PCR Reverse Primer (10 μM) | 1.0 μl |
| cDNA | 1.0 μl |
| Rnase free dH$_2$O | 4.5 μl |
| Total | 15.0 μl |

Use conditions of PCR are as follows:
Stage 1: initial denaturation at 95° C. for 1 min.
Stage 2: PCR reaction at 95° C. for 15 sec; for example, at 60° C. for 30 sec for 40 Cycles; and at 72° C. for 30 sec.
Stage 3: dissociation curve analysis at 65 to 95° C., 0.5° C./5s.

Primer sequences of genes to be detected are shown in Table 3:

TABLE 3

| Primer sequence | | | | | |
|---|---|---|---|---|---|
| Genename | | Forward primer | | | Reverse primer |
| Rat Fxr | SEQ ID No. 1 | TGGACTCATACAG CAAACAGAGA | SEQ ID No. 2 | | GTCTGAAACCCTGG AAGTCTTTT |
| Rat Shp | SEQ ID No. 3 | CCTGGAGCAGCCC TCGT | SEQ ID No. 4 | | AACACTGTATGCAA ACCGAGGA |
| Rat Acta2 | SEQ ID No. 5 | GCTCCATCCTGGC TTCTCTA | SEQ ID No. 6 | | TAGAAGCATTTGCG GTGGAC |
| Rat Gapdh | SEQ ID No. 7 | AACGGCACAGTC AAGGCTGA | SEQ ID No. 8 | | ACGCCAGTAGACTC CACGACAT |
| Mouse Fxr | SEQ ID No. 9 | GCACGCTGATCAG ACAGCTA | SEQ ID No. 10 | | CAGGAGGGTCTGTT GGTCTG |
| Mouse Shp | SEQ ID No. 11 | GTACCTGAAGGG CACGATCC | SEQ ID No. 12 | | GTGAAGTCTTGGAG CCCTGGT |
| Mouse Acta2 | SEQ ID No. 13 | GCACCCAGCATG AAGATCAAG | SEQ ID No. 14 | | TCTGCTGGAAGGTA GACAGCGAAG |
| Mouse Gapdh | SEQ ID No. 15 | TTGATGGCAACAA TCTCCAC | SEQ ID No. 16 | | CGTCCCGTAGACAA AATGGT |

2.3 SUMOylation ELISA detection kit

After cell nuclear proteins were extracted according to specification requirements of an ELISA detection kit, primary antibodies and nuclear proteins of a cell sample were incubated for 60 min at the room temperature in a plate hole. SUMO specific detection antibodies were then supplemented and added according to the specification requirements. A color sensitizer was further added for color development. Then, absorbance at 655 nm was fast read. Relative quantitative analysis was performed.

Figure 1B:
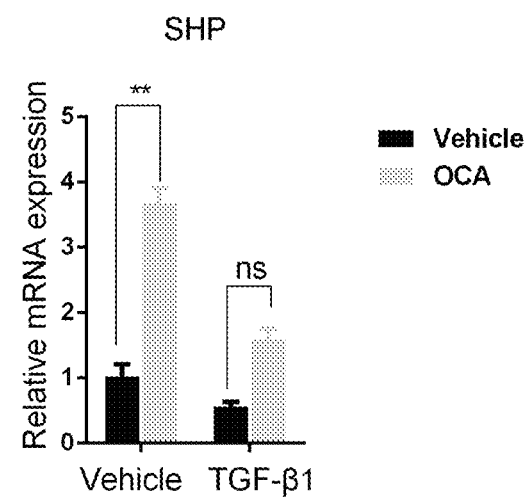
FIG. 1B is mRNA level analysis of Shp in quiescent (vehicle) and activated (TGF-β) HSCs treated with OCA.
Figure 1C:
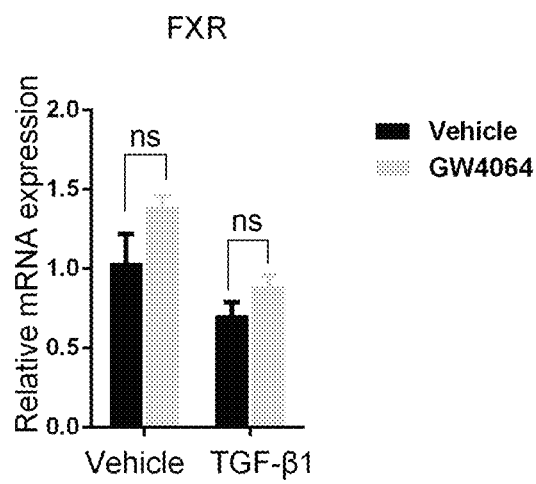
FIG. 1C is mRNA level analysis of Fxr in quiescent (vehicle) and activated (TGF-β) HSCs treated with GW4064.
Figure 1D:
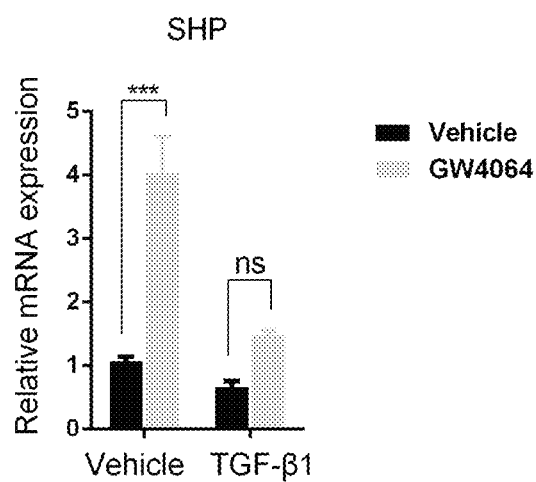
FIG. 1D is mRNA level analysis of Shp in quiescent (vehicle) and activated (TGF-β) HSCs treated with GW4064.
Figure 1E:
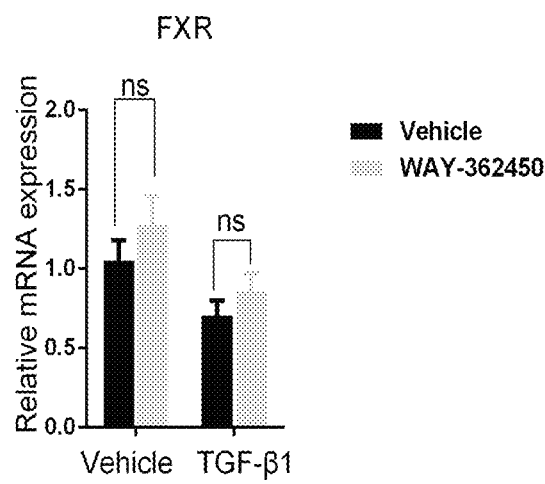
FIG. 1E is mRNA level analysis of Fxr in quiescent (vehicle) and activated (TGF-β) HSCs treated with WAY-362450.
Figure 1F:
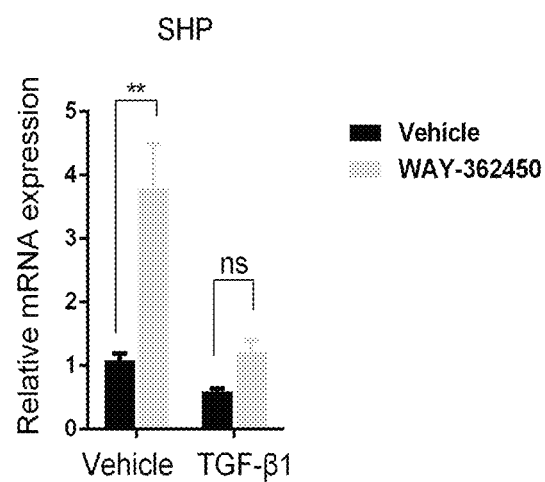
FIG. 1F is mRNA level analysis of Shp in quiescent (vehicle) and activated (TGF-β) HSCs treated with WAY-362450. *P<0.05. P<0.01. * P<0.001.

3. Experiment Results 3.1 Reduced responsiveness of activated HSCs to the FXR agonist In cultured HSCs in vitro, activation of the HSCs was promoted by incubation with TGF-$\beta$1. According to results of real-time RT-PCR (FIGS. 1A-F), the capability of the FXR agonist in regulating FXR downstream target genes is reduced in HSC-T6 cell in activated state caused by TGF-$\beta$1 incubation. In quiescent cells, FXR agonists OCA, GW4064 and WAY-362450 could significantly up-regulate the mRNA level of Shp, an FXR target gene (FIG. 1B, FIG. 1D, and FIG. 1F). In the activated state, none of the FXR agonists OCA, GW4064 and WAY-362450 could significantly up-regulate the mRNA level Shp (FIG. 1A, FIG. 1B, and FIG. 1F).

3.2 Improved SUMOylation level of FXR proteins in activated HSCs

According to ELISA kit detection aiming at the SUMOylation level (FIG. 2), the SUMOylation level of FXR proteins in the activated HSC-T6 cells caused by TGF-$\beta$1 incubation was significantly elevated.

Embodiment 2

Effect of SUMO Inhibitor on FXR Pathway in In-vitro HSCs

1. Experiment Materials

SUMO inhibitors of spectinomycin (SP) and ginkgolic acid (GA) were purchased from MCE Company.

Other experiment materials were the same as those in Embodiment 1.

2. Experiment Methods 2.1 HSC-T6 cell line culture and modeling

Specific methods were the same as those in section 2.1 in Embodiment 1.

2.2 RT-PCR

Specific methods were the same as those in section 2.2 in Embodiment 1.

2.3 SUMOylation ELISA detection kit

Specific methods were the same as those in section 2.3 in Embodiment 1.

Figure 3:
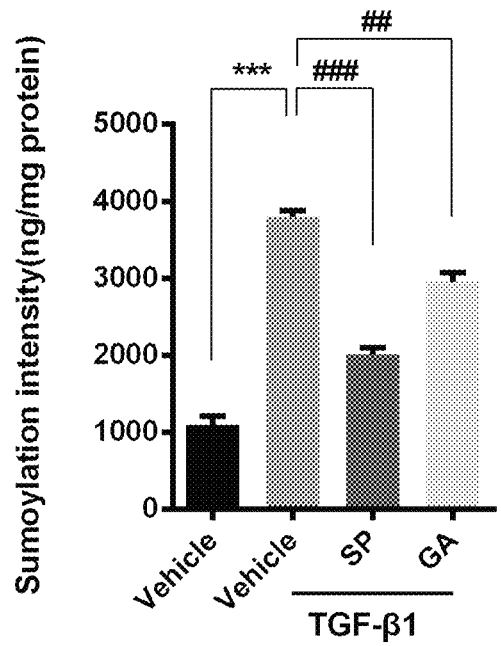
FIG. 3 is SUMOylation level analysis of FXR proteins in activated HSCs treated with
SUMO inhibitors SP and GA. ***P<0.001. ##P<0.01. ###P<0.001.

3. Experiment Results 3.1 SUMO inhibitors inhibited SUMOylation of FXR proteins in activated HSCs Through detection by SUMOylation ELISA kits, it was found that SUMOylation inhibitors SP and GA could significantly reduce the SUMOylation level of FXR proteins in activated HSCs (FIG. 3).

Figure 4A:
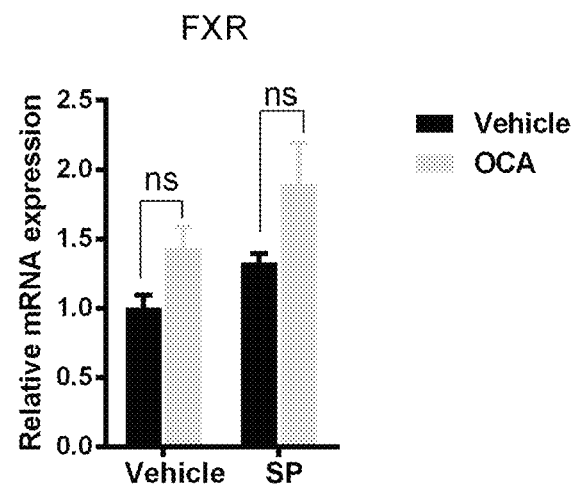
FIG. 4A is mRNA level analysis of Fxr in activated HSCs treated with a combination of OCA and SP.
Figure 4B:
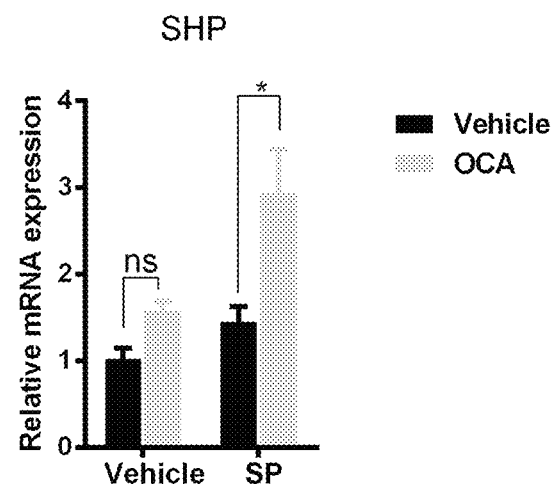
FIG. 4B is mRNA level analysis of Shp in activated HSCs treated with a combination of
OCA and SP.
Figure 4C:
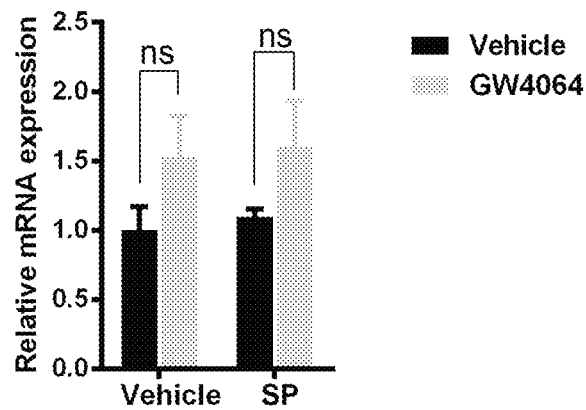
FIG. 4C is mRNA level analysis of Fxr in activated HSCs treated with a combination of GW4064 and SP.
Figure 4D:
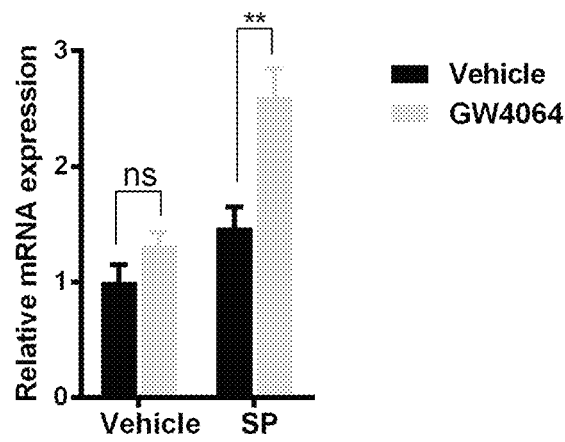
FIG. 4D is mRNA level analysis of Shp in activated HSCs treated with a combination of GW4064 and SP.
Figure 4E:
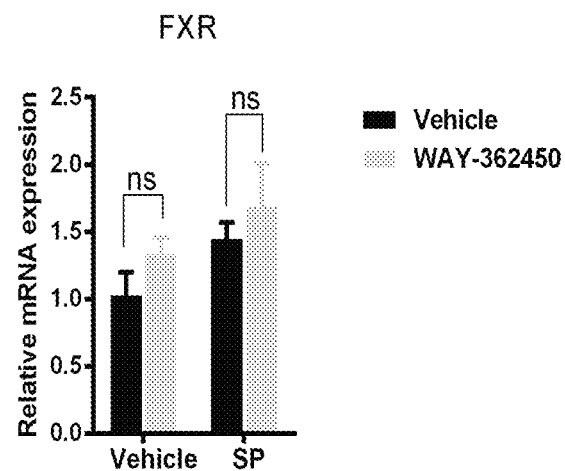
FIG. 4E is mRNA level analysis of Fxr in activated HSCs treated with a combination of WAY-362450 and SP.
Figure 4F:
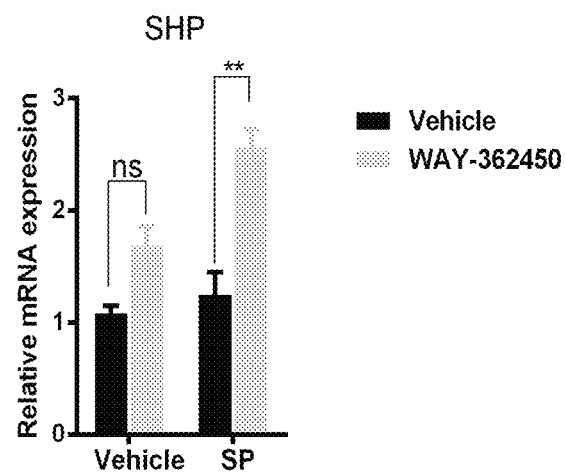
FIG. 4F is mRNA level analysis of Shp in activated HSCs treated with a combination of WAY-362450 and SP.
Figure 4G:
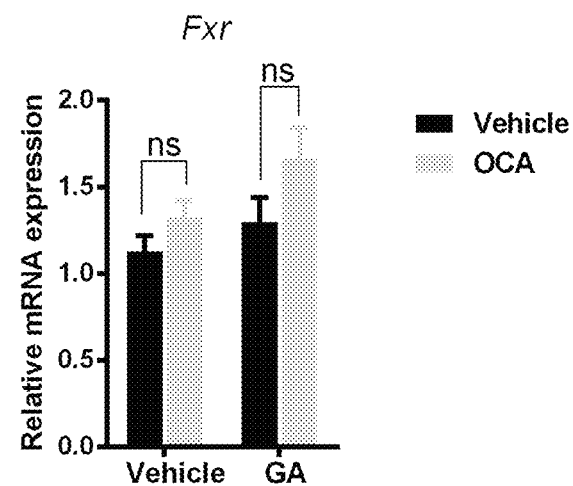
FIG. 4G is mRNA level analysis of Fxr in activated HSCs treated with a combination of OCA and GA.
Figure 4H:
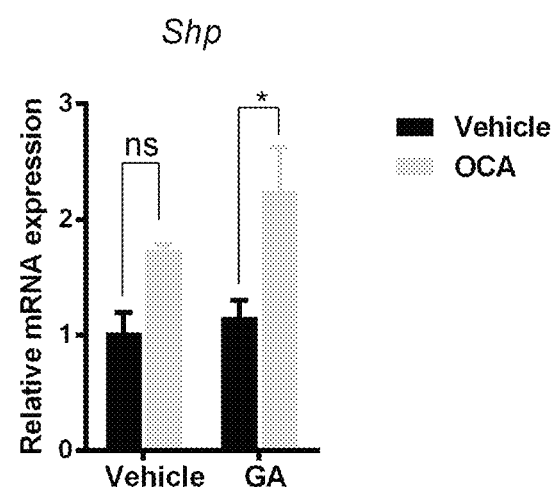
FIG. 4H is mRNA level analysis of Shp in activated HSCs treated with a combination of OCA and GA. ns $P>0.05$. *$P<0.05$. **$P<0.01$.
Figure 5A:
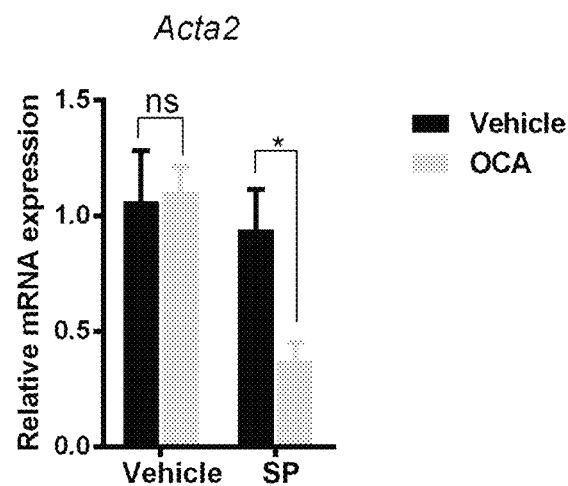
FIG. 5A is mRNA expression level analysis of Acta-2 treated with a combination of OCA and SP.
Figure 5B:
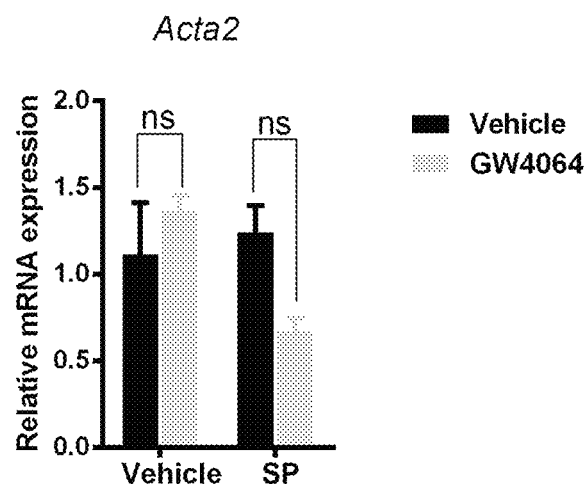
FIG. 5B is mRNA expression level analysis of Acta-2 treated with a combination of GW4064 and SP.
Figure 5C:
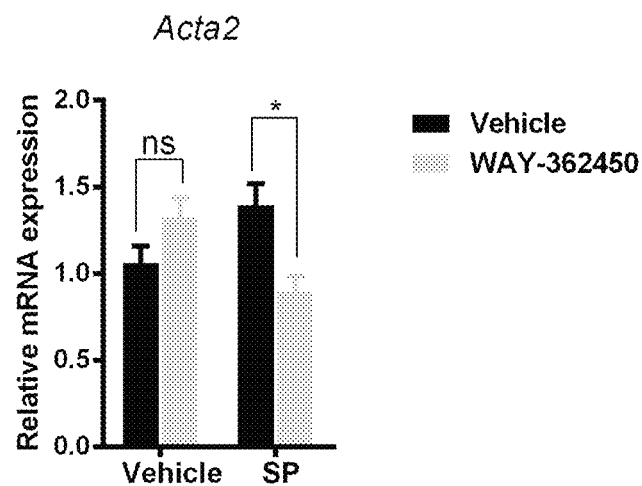
FIG. 5C is mRNA expression level analysis of Acta-2 treated with a combination of WAY-362450 and SP.
Figure 5D:
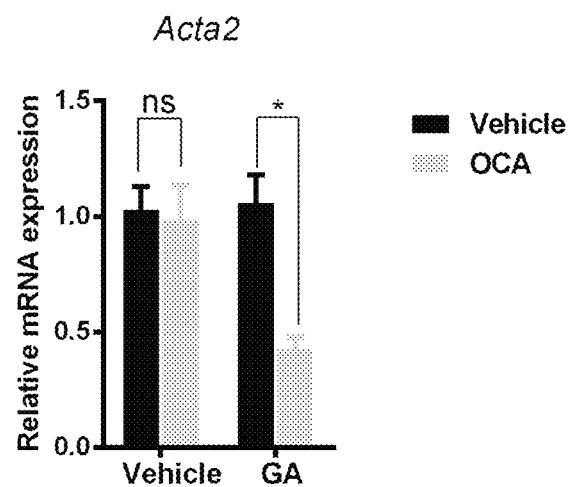
FIG. 5D is mRNA expression level analysis of Acta-2 treated with a combination of OCA and GA. ns $P>0.05$. *$P<0.05$.

3.2 SUMO inhibitors improved the responsiveness of activated HSCs to FXR agonists In Embodiment 1, it was found that in activated HSCs, FXR agonists OCA, GW4064 and WAY-362450 lost their regulation effects on the FXR signaling pathway, manifested by loss of an induction effect on Shp. In the study of this section, the regulation effect of the FXR agonist on the FXR signaling pathway in the presence or absence of SUMO inhibitors was investigated. According to the results of RT-PCR (FIGS. 4A-H), FXR agonists OCA, GW4064 and WAY-36250 significantly up-regulated the mRNA expression of Shp in the presence of SUMO inhibitor SP in activated HSCs (FIG. 4B, FIG. 4D, and FIG. 4F). Similar phenomenon was observed in the presence of another SUMO inhibitor GA (FIG. 4H).

3.3 SUMO inhibitors enhanced the inhibitory effect of FXR agonists on activation of HSCs Above results show that SUMO inhibitors can inhibit the SUMOylation of FXR, and further enhance the regulation effects of the FXR agonists on the FXR signaling in activated HSCs. Then, the effect of SUMO inhibitors on HSC activation resistance of FXR agonist was investigated. Identically, according to the results of RT-PCR (FIG. 5), after administration of SP to the activated HSCs, administration of FXR agonist OCA, GW4064 and WAY36250 significantly reduced the expression of a fibrotic-related gene Acta2 in hepatic stellate cells; similarly, after administration of the GA to the activated HSCs, OCA could significantly inhibit expression of the Acta2. Above results show that the SUMO inhibitors SP and GA can reduce the SUMOylation level of the FXR proteins, and enhance the inhibitory effect of FXR agonists on the expression of fibrosis-related genes in activated HSCs, thereby improving the anti-fibrotic efficacy.

Embodiment 3

Effect of SUMO Inhibitor on FXR Pathway Under Liver Fibrosis State of Mice

1. Experiment Materials

Experiment mice (C57BL/6) were purchased from Comparative Medicine Centre of Yangzhou University.

$CCl_4$ was purchased from Shanghai Lingfeng Chemical Reagent Company, and mineral oil was purchased from Sigma-Aldrich Company.

Other experiment materials were the same as those in Embodiment 1.

2. Experiment Methods 2.1 Effect of a combination of SUMO inhibitor and OCA on $CCl_4$-induced liver fibrosis After animal adaptive feeding for one week, a total of 40 mice were randomly divided into 5 groups with 8 mice in each group. A control group, a model group, an OCA single-administration group, an SP single-administration group and an OCA+SP co-administration group were included. The model group received intraperitoneal injection of $CCl_4$ (20%, dissolved in mineral oil). In the control group, a vehicle (mineral oil) with corresponding volume was administrated twice a week for 4 weeks. Mice received intraperitoneal intragastric administration of OCA at a dosage of 1.5 mg/kg once a day from the third week for two weeks after modeling. Additionally, in the OCA+SP co-administration group, SP was subcutaneously injected at a dosage of 200 mg/kg/day from the first week. At the end of the administration periods, the mice were killed, and the livers were isolated and stored for use.

2.2 RT-PCR

Specific methods were the same as those in section 2.2 in Embodiment 1.

2.3 Liver clinicopathologic analysis

After being fixed in 4% paraformaldehyde, some liver tissues were sent to Wuhan Servicebio Technology Co., Ltd. (Wuhan, China) for double-blind analysis and detection. A detection item was Sirius red staining analysis.

Figure 6A:
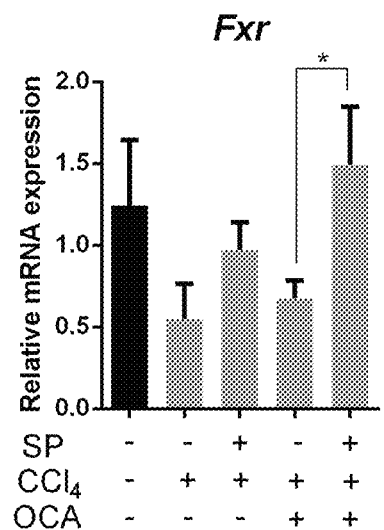
FIG. 6A is mRNA expression level analysis of Fxr.
Figure 6B:
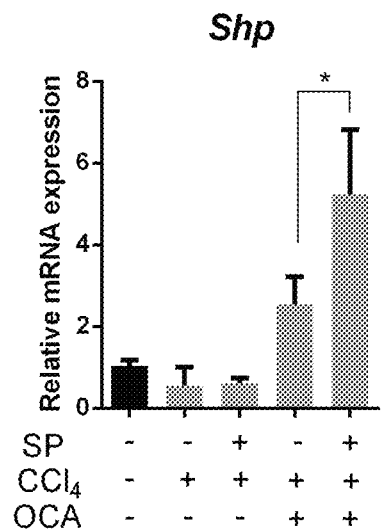
FIG. 6B is mRNA expression level analysis of Shp. *$P<0.05$.

3. Experiment Results 3.1 Enhancement of regulation effects of OCA on FXR pathway of fibrotic mice by SUMO inhibitor Through RT-PCR experiments, mRNA relative expression of an FXR downstream gene in liver tissues was investigated (FIG. 6). It was found that mRNA level of the FXR downstream gene significantly increased by OCA treatment after combined use with SP. It showed that SUMOylation inhibitors could enhance the agonistic effect of the FXR agonist OCA on the FXR pathway in fibrotic mice.

Figure 2:
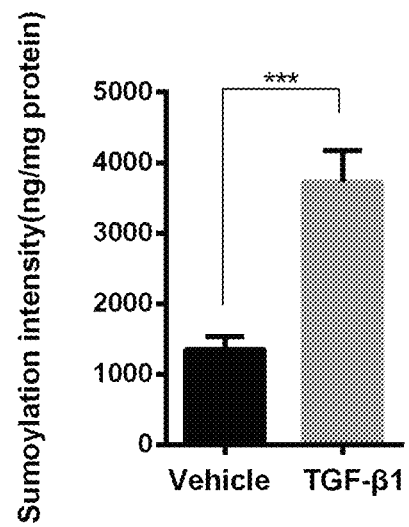
FIG. 2 is SUMOylation level analysis of FXR proteins after activation of HSCs. ***P<0.001.
Figure 7A:
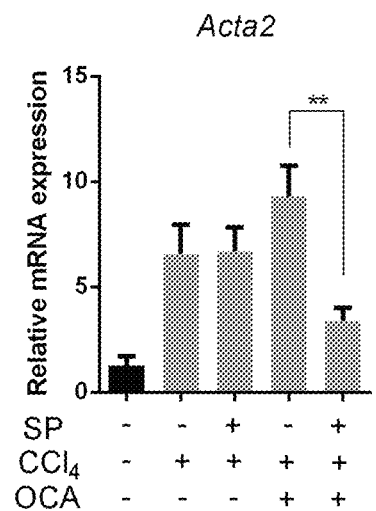
FIG. 7A is mRNA expression level analysis of Acta-2. **$P<0.01$.
Figure 7B:
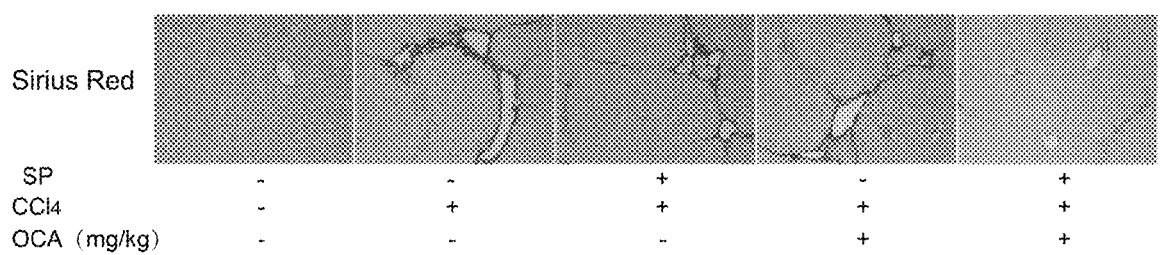
FIG. 7B is liver Sirius red staining.
Note: in all figures of the present invention, P value below 0.05 indicates a statistical difference.

3.2 Capability of SUMO inhibitor SP to enhance anti-hepatic fibrosis efficacy of OCA According to the expression investigation of fibrosis-related genes in liver tissues in RT-PCR experiments and staining results of liver pathological analysis, it was found that the anti-fibrotic efficacy of the OCA is significantly improved in the presence of SUMO inhibitor SP. The RT-PCR results showed that the expression of the major fibrosis gene Acta2 in the liver tissues in the co-administration group (SP+OCA) was also significantly reduced compared with that of the single administration group (FIG. 7A). Additionally, Sirius red staining results showed that only few of red collagen fibers in the liver of the control group were stained while slices in the model group and OCA single-administration group contained a great number of red collagen fibers due to hepatotoxicity, but after OCA and SP co-administration was adopted, red collagen fiber hyperplasia in the liver was reduced (FIG. 7-2).

It can be concluded from the above embodiments that the hepatic stellate cells in activated state lose the responsiveness to FXR agonist, thus FXR agonist does not have an effect in inhibiting the activation of hepatic stellate cells. After the FXR agonist and SUMO inhibitor are compounded according to the present invention, hepatic stellate cells in activated state restore the responsiveness to FXR agonist. More importantly, this composition proposed in this invention exert excellent inhibitory effect on the activation of hepatic stellate cells in activated state, reducing the production of collagen fibers and thus inhibit progress of liver fibrosis.

The present invention only describes preferred implementations above. It should be noted that, for those ordinarily skilled in the art, various improvements and adaptations can be made without departing from the principles of the present invention, and such modifications and adaptations shall be deemed to be within the protection scope of the present invention.

What is claimed is:

1. A composition for treating hepatic fibrosis comprising a FXR agonist and a SUMO inhibitor.

2. The composition according to claim 1, wherein the FXR agonist is one or more selected from the group consisting of obeticholic acid, GW4064 and WAY-362450.

3. The composition according to claim 1, wherein the SUMO inhibitor is spectinomycin or/and ginkgolic acid.

4. A method for treating hepatic fibrosis comprising a step of administrating to a subject in need a therapeutically effective amount of the composition of claim 1.

5. The method according to claim 4, wherein activation of hepatic stellate cells is inhibited in the subject.

6. The method according to claim 4, wherein deposition of collagen fibers is reduced in the subject.

7. A pharmaceutically acceptable medicine comprising the composition of claim 1 as active ingredient, and a pharmaceutically acceptable carrier.

8. The pharmaceutically acceptable medicine according to claim 7, wherein the pharmaceutically acceptable medicine is made in a form selected from a group consisting of a tablet, a capsule, a granule, a pill, powder and an injection.

* * * * *